United States Patent [19]
Madsen, Jr. et al.

[11] Patent Number: 5,776,173
[45] Date of Patent: Jul. 7, 1998

[54] PROGRAMMABLE INTERFERENTIAL STIMULATOR

[76] Inventors: Ronald E. Madsen, Jr., 2094 E. Lamborne Ave., Salt Lake City, Utah 84109; Matt Carlson, 3142 E. 9800 South, Sandy, Utah 84092

[21] Appl. No.: 869,418

[22] Filed: Jun. 4, 1997

[51] Int. Cl.$^6$ .................................................. A61N 1/08
[52] U.S. Cl. ............................................................ 607/67
[58] Field of Search ............................................. 607/67

[56] References Cited

U.S. PATENT DOCUMENTS

| | | |
|---|---|---|
| 4,848,347 | 7/1989 | Hall . |
| 5,161,530 | 11/1992 | Gamble . |
| 5,324,317 | 6/1994 | Reiss . |
| 5,512,057 | 4/1996 | Reiss . |
| 5,549,656 | 8/1996 | Reiss . |

Primary Examiner—William E. Kamm
Attorney, Agent, or Firm—Terrance L. Siemens

[57] ABSTRACT

The present invention features an portable, programmable interferential stimulator for the administering of neuromuscular electrotherapy to a human subject. A number of pre-programmed modulation modes are easily selectable using a keypad and a self-contained alpha-numeric display. Compliance data including the number, length and mode of usage sessions is captured and stored internally in non-volatile memory. Automatic shut-off at the end of a therapy session is also included. An optional bi-directional, serial interface allows for loading custom programs from an external computer session into the instant stimulator. The interface also allows for uploading compliance data to the external computer for analysis or archiving.

18 Claims, 6 Drawing Sheets

PROGRAMMABLE INTERFERENTIAL STIMULATOR

FIELD OF THE INVENTION

The present invention relates to an interferential stimulator for the administration of neuromuscular electrotherapy to a human subject, and more specifically to a portable, programmable interferential stimulator with self-contained usage monitoring.

BACKGROUND OF THE INVENTION

The use of neuromuscular electro-stimulation for the relief of pain, reduction of edema, the stimulation of muscle, as well as other therapeutic purposes is well known and a wide variety of apparatuses have been developed to administer such therapy. In general, a controlled electrical signal is applied to one or more pairs of electrodes attached to a patient's skin at or near the body area requiring stimulation or treatment. The frequency, amplitude, waveshape and pulse duration of the applied electrical signal may each be controlled to provide the desired response in the patient. Recently, electro-stimulation units employing interferential techniques have been introduced. These interferential units rely on the use of multiple, independent pairs of electrodes, each electrode pair receiving an alternating current signal at a different frequency or phase. By controlling the frequency and/or phase relationship of the electrical signals, the target stimulation area may be broadened as the stimulating currents are rotated or "vectored". Many schemes presently exist for selecting the frequency and amplitude of these currents. A ramped signal is often used to vary the beat frequency (the difference between the two original frequencies caused by hetrodyning) to values such as between 1 Hz and 150 Hz. The ramp duration may also be varied to achieve a desired therapeutic outcome, a ramp time of about 20 seconds being typically used. The controls for adjusting the aforementioned parameters are usually analog, often single-turn potentiometers. While every attempt is made by manufacturers of stimulator equipment to provide controls which can not be accidentally adjusted, all too often the controls are easily changed. In the best case, when the controls are accidentally changed, the patient no longer receives the therapy deemed optimum for the condition being treated. In the worst case, uncomfortable electrical shock may result from the maladjustment of one or more controls. In addition, portable electro-stimulation units available heretofore have had limited flexibility in the variety of treatment modalities available. Setup has been difficult and, even after a desired treatment modality has been established, the setup may be easily, inadvertently altered. In addition, a prescribing therapist has had no way to know whether or not a patient has complied with the ordered treatment regime.

DISCUSSION OF THE PRIOR ART

Several electro-stimulation devices have previously been described. U.S. Pat. No. 4,848,347 for INTERFERENTIAL ELECTRICAL CURRENT THERAPY SYSTEMS AND METHODS; issued Jul. 18, 1989 to Duane O. Hall teaches an interferential electro-stimulation device. Signals from a pair of oscillators are phase shifted, mixed, amplified and applied to two electrode pairs. A rudimentary processor is used to control the oscillators, phase shifters and mixers. Unlike the interferential stimulator of the present invention, the Hall device does not appear to be a portable unit adapted for ease of use by the patient being treated. Neither does the Hall device provide a variety of preprogrammed treatment modalities nor have the facility to load custom operational programs via an optional serial interface. Finally, the Hall apparatus does not provide any means for monitoring usage of the apparatus by a patient as does the stimulator of the present invention.

Another interferential stimulation device is disclosed in U.S. Pat. No. 5,161,530; for INTERFERENTIAL THERAPY EMPLOYING SWITCHING MECHANISM; issued Nov. 10, 1992 to James. J. Gamble. The Gamble apparatus attempts to increase the region of stimulation by utilizing at least one extra electrode in addition to the traditional one or two pairs of electrodes found in the prior art. There is no indication that the Gamble apparatus may be provided in a lightweight, self-contained package for portable use. In contradistinction, the instant stimulator features a small, lightweight package for ease of use by the patient. Either bipolar or quadrapolar modalities may be switch-selected. Also, unlike the Gamble apparatus, compliance data is compiled automatically and stored by the instant stimulator. With the addition of an optional serial interface, the stimulator of the present invention allows the loading of a custom program or the uploading of compliance data to an external computer.

Still another stimulator is taught in U.S. Pat. No. 5,324, 317; issued Jun. 28, 1994 to Hans W. Reiss. The Reiss stimulator features a small, portable package. Unlike the programmable, microprocessor-controlled circuitry of the instant stimulator, the Reiss stimulator has strictly manually adjusted, potentiometer-type analog controls. The Reiss circuitry is all analog (i.e., not microprocessor controlled) thereby limiting any preprogrammed treatment modalities. Neither is there, in the Reiss stimulator, any way to track patient usage. In contradistinction, the digital controls of the microprocessor-controlled stimulator of the invention allow a wide variety of pre-programmed treatment modalities. Also, unlike Reiss, the instant stimulator features usage tracking for monitoring a patient's compliance to the prescribed therapy. An automatic shut-off at the end of a programmed treatment and an optional bi-directional serial interface are also featured in the instant stimulator.

Yet another interferential stimulator is described in U.S. Pat. No. 5,512,057; for INTERFERENTIAL STIMULATOR FOR APPLYING LOCALIZED STIMULATION; issued Apr. 30, 1996 also to Hans W. Reiss. The Reiss '057 apparatus features somewhat more extensive user controls than the Reiss '317 stimulator described above. The controls of the '057 stimulator are, however, also manual and analog unlike the digital controls featured in the instant stimulator. The '057 stimulator, unlike the stimulator of the present invention, has no method for storing patient compliance data. The instant stimulator, on the other hand, features pre-programmed treatment regimes with automatic shut-off at the end of the treatment. In addition, the optional serial interface present on the instant stimulator allows the loading of special treatment programs into the stimulator from an external computer or controller as well as the uploading of compliance data from the stimulator for later analysis or patient history storage.

Finally, U.S. Pat. No. 5,549,656; for COMBINATION NEUROMUSCULAR STIMULATOR AND ELECTROMYOGRAPH SYSTEM; issued Aug. 27, 1996 to Hans W. Reiss features an interferential stimulator for table top use. The controls are analog. In addition to the stimulator function an electromyograph function for monitoring a patients response to the provided stimulation is also included. The electrodes are duplexed between stimulation delivery and pickup functions. In contradistinction, the interferential stimulator of the present invention features a light-weight, portable design. All controls of the instant stimulator are digital. The instant stimulator also features a usage monitoring function whereby a patient's use of the device is recorded for later readout by the prescribing practitioner. The instant stimulator also may be equipped with an optional serial interface for allowing programming of the unit or uploading of compliance data to an external computer.

It is therefor an object of the invention to provide an interferential stimulator overcoming the aforementioned and other shortcomings of the prior art by providing a interferential stimulator in a light-weight, portable package for ease of use by the patient receiving the electro-stimulation therapy. The instant stimulator may be readily attached to a belt or otherwise attached to the patient's person thereby allowing for mobility of the patient during the course of the electro-stimulative therapy.

It is a further object of the invention to provide an interferential stimulator having digital controls and an alpha-numeric display panel for ease of use and accuracy in setting up the stimulator. The present invention overcomes the previously described problems of accidental maladjustment of potentiometer-type controls found in most stimulators of the prior art.

It is yet another object of the invention to provide an interferential stimulator capable of logging usage of the stimulator. User compliance information may be retrieved by the prescribing practitioner.

It is yet a further object of the invention to provide an interferential stimulator which is microprocessor-based and has a selection of preprogrammed treatment modalities easily selected by the prescribing practitioner or the patient.

It is a still further object of the invention to provide a stimulator with automatic shut-off at the conclusion of a treatment session.

It is an additional object of the invention to provide a serial interface to allow loading special treatment programs into the stimulator and/or to upload patient usage or compliance data from the stimulator into an external computer.

SUMMARY OF THE INVENTION

The present invention features a light-weight, portable microprocessor-based, interferential electrical stimulator for the administration of neuromuscular electrotherapy to a living patient. The instant interferential stimulator is equipped with digital controls and a two row by twelve column LCD alpha-numeric display to allow easy setup of multiple, complex therapy regimes with selectable, automatic shut-off at the termination of the program. A self-contained usage monitoring subsystem stores patient usage/compliance information for readout using the LCD display by the prescribing professional. Finally, an optional serial interface allows the loading of special treatment programs from an external computer into the stimulator. The serial interface also allows the uploading of compliance data from the stimulator into the computer for analysis and/or archiving.

BRIEF DESCRIPTION OF THE DRAWINGS

A complete understanding of the present invention may be obtained by reference to the accompanying drawings, when taken in conjunction with the detail description thereof and in which.

DESCRIPTION OF THE PREFERRED EMBODIMENT

Generally speaking this invention relates to an interferential electro-stimulation device and, more particularly to a novel, portable, microprocessor-based, digitally-controlled electro-stimulator capable of multi-mode operation for the delivery of electric current therapy to a patient. The instant stimulator supports either bipolar or quadrapolar operation utilizing, respectively, one or two pairs of electrodes attached to a patient's body proximate the area requiring therapy. A wide range of treatment modalities are easily selected by means of the digital controls and the LCD display. Usage information is stored in internal, non-volatile memory for later readout by the prescribing practitioner.

Figure 1:
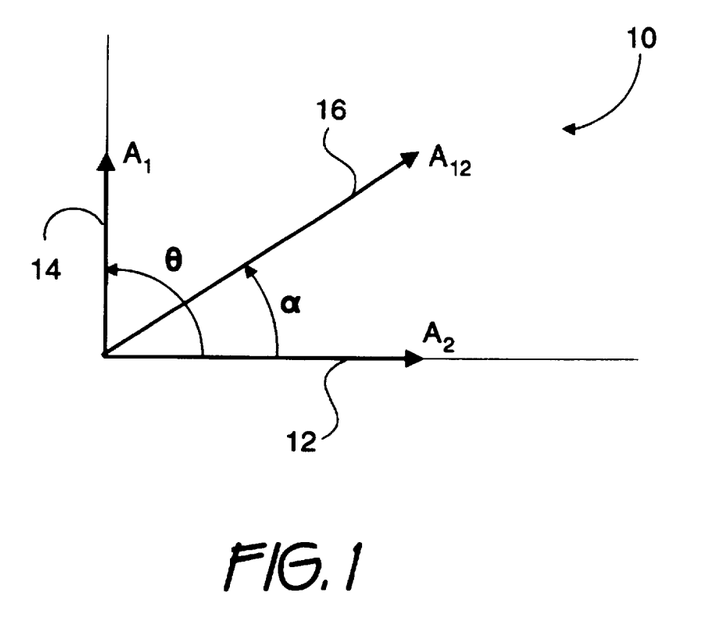
FIG. 1 is a vector diagram of two interacting AC signals.

Interferential electro-therapy receives its name from the interference between two electrical signals of different frequencies and/or phases. When two such alternating current (AC) electrical signals are algebraically combined (i.e., mixed), there results two additional ac signals whose frequencies are the sum and difference of the frequencies of the original two signals. The resultant signals will also have a phase angle related to the phase angles of the original two signals. Referring first to FIG. 1, there is shown a vector diagram 10 of two ac electrical signals (vectors) 12 and 14, with a phase angle $\ominus$ therebetween. Signal 14 is said to be 90° "out-of-phase" with respect to signal 12 (i.e., signal/vector 14 is rotated 90° with respect to signal 12). Signal 12 has an amplitude $A_1$ and signal 14 has an amplitude $A_2$. A resultant signal 16 is shown at a phase angle $\alpha$ with respect to signal 14. The amplitude of signal 16 may be determined using simple trigonometric equations for a right triangle:

$$C^2 = A^2 + B^2, \text{ or its derivative:}$$

$$C = \sqrt{A^2 + B^2},$$

where A represents amplitude $A_1$ of signal 14; B represents amplitude $A_2$ of signal 12; and C represents the amplitude $A_{12}$ of resultant signal (vector) 16. By varying the phase angle $\ominus$ between the two original signals 12 and 14, the resultant signal 16 may be made to rotate through 360° with respect to an original signal. By controlling the amplitude of one or both of signals 12 and 14, the amplitude of resultant signal 16 may also easily be controlled. Amplitude $A_{12}$ is referred to as the "head" of vector 16. In interferential therapy, the position of vector head $A_{12}$ is closely related to a physical region where electrical stimulation is being applied to a patient's body. As signal/vector 16 is rotated, therapy may be applied to an essentially circular region of the body. All interferential electro-stimulation devices rely on the "rotating" of a resultant vector by manipulation of the frequency and/or phase components of one or more pairs of electrical signals generated within the stimulation apparatus.

Using the front-panel mode selection keys described in detail hereinbelow, the operator may select one of a number of pre-programmed output signal modulation modes. These modes are identified by three-character codes which are displayed on a front-panel, liquid-crystal display. These modulation modes are implemented in microcontroller software. Thus, the number of available modulation modes and the specifications for each mode can be customized as required. In the preferred embodiment, eleven modulation modes have been defined. The three-character code identifying each modulation mode and a description of each of these modes is presented hereinbelow.

"CON"—STEADY STATE

No automatic modulation of either output amplitude or output frequency is provided.

"66R"—FREQ-RAMP 6/6

Ramp the second-channel output frequency up above the dialed-in value during a six-second interval, then ramp it back down through and below the dialed-in frequency during another six second interval.

"11R"—FREQ-RAMP 1/1

Ramp the second-channel output frequency up above the dialed-in value during a one-second interval, then ramp it back down through and below the dialed-in frequency during another one-second interval.

"66A"—FREQ-SQUARE 6/6

Abruptly raise the second-channel output frequency up above the dialed in value and hold it there during a six second interval, then abruptly lower it down through and below the dialed-in frequency and hold it there during another six-second interval.

"11A"—FREQ-SQUARE 1/1

Abruptly raise the second-channel output frequency up above the dialed in value and hold it there during a one-second interval, then abruptly lower it down through and below the dialed-in frequency and hold it there during another one-second interval.

"11S"—AMP-ON-OFF 1/1

Abruptly drop the amplitude of both outputs to zero and hold them there for one second, then abruptly raise them to the dialed-in amplitude value and hold them there for another second.

"66S"—AMP-ON-OFF 6/6

Abruptly drop the amplitude of both outputs to zero and hold them there for six seconds, then abruptly raise them to the dialed-in amplitude value and hold them there for another six seconds.

"5_S"—AMP-RAMP 5/15

During an interval of approximately 1.5 seconds, ramp the amplitude of both channels up from zero to the dialed-in amplitude value, then hold them there for 5 seconds, then, during another interval of approximately 1.5 seconds, ramp the amplitudes down from the dialed-in value to zero, then hold them there for 15 seconds.

"12S"—AMP-RAMP 12/36

During an interval of approximately 1.5 seconds, ramp the amplitude of both channels up from zero to the dialed-in amplitude value, then hold them there for 12 seconds, then, during another interval of approximately 1.5 seconds, ramp the amplitudes down from the dialed-in value to zero, then hold them there for 36 seconds.

"15S"—AMP-RAMP 15/45

During an interval of approximately 1.5 seconds, ramp the amplitude of both channels up from zero to the dialed-in amplitude value, then hold them there for 15 seconds, then, during another interval of approximately 1.5 seconds, ramp the amplitudes down from the dialed-in value to zero, then hold them there for 45 seconds

"20S"—AMP-RAMP 20/40

During an interval of approximately 1.5 seconds, ramp the amplitude of both channels up from zero to the dialed-in amplitude value, then hold them there for 20 seconds, then, during another interval of approximately 1.5 seconds, ramp the amplitudes down from the dialed-in value to zero, then hold them there for 40 seconds.

The optional serial interface discussed in detail hereinbelow allows for a virtually unlimited number of complex modulation modes to be loaded from an external controller or computer.

Figure 2:
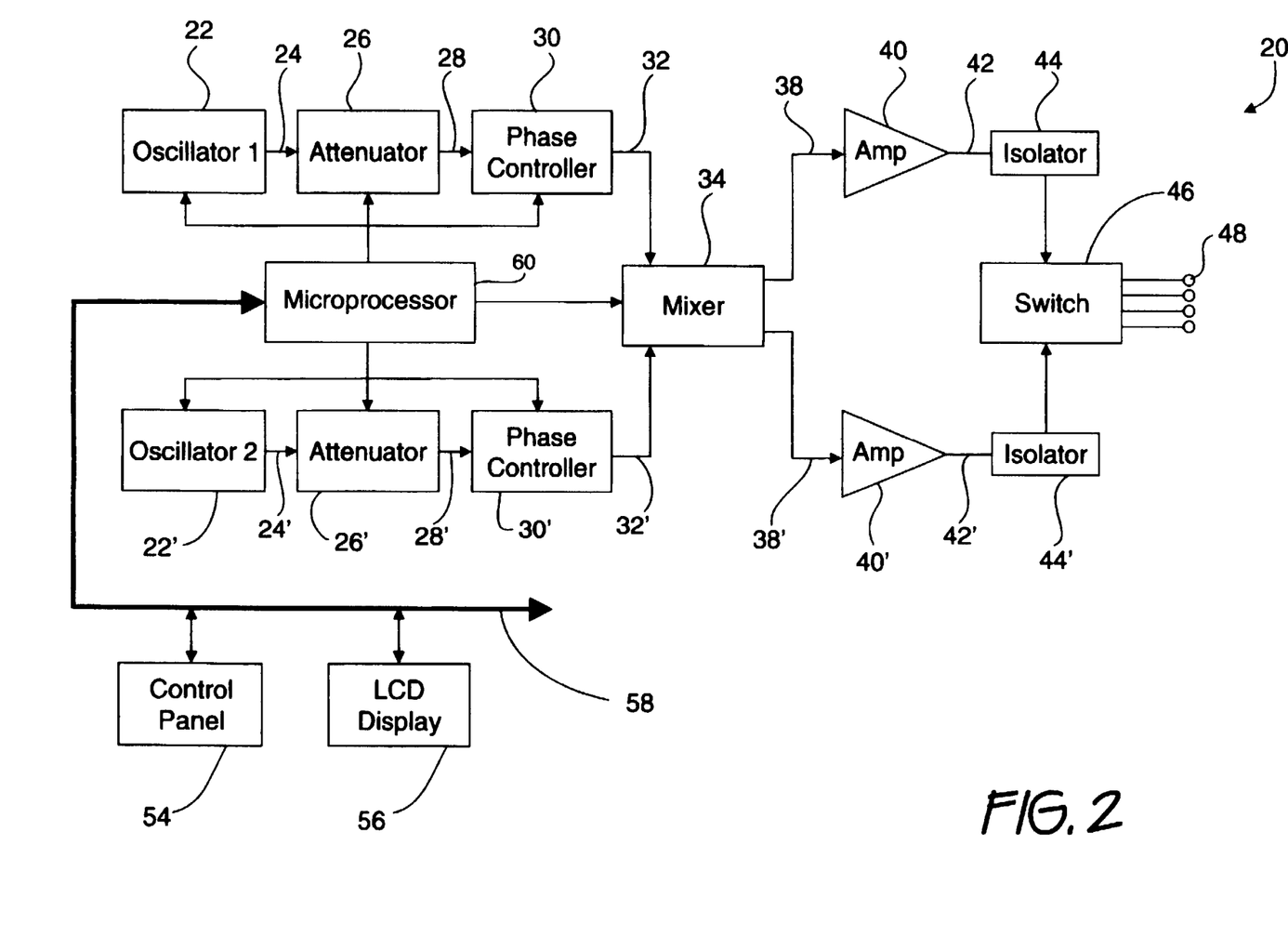
FIG. 2 is a simplified functional block diagram of a typical interferential stimulator.

Referring now to FIG. 2, there is shown a simplified functional block diagram 20 of a typical microprocessor-controlled interferential electro-stimulator. A first oscillator 22 generates, a first output signal 24 having a first frequency. First output signal 24 is applied to the input of attenuator 26. Attenuator 26 provides a first attenuated output signal 28 which is applied to the input of phase controller 30. Phase controller 30, in turn, generates a first phase-controlled output signal 32 which is next applied to one input of mixer 34. A second oscillator 22' generates a second output signal 24' having a second frequency. Second output signal 24' is applied to the input of attenuator 26'. Attenuator 26' provides a second attenuated output signal 28' which is applied to the input of phase controller 30'. Second phase controller 30 generates a second phase-controlled output signal 32' which is applied to a second input of mixer 34.

Oscillators 22, 22', attenuators 26, 26', and phase controllers 30, 30' are all operatively connected to microprocessor 60 which provides control signals to each component from instructions contained within the microprocessor's memory (not shown).

Mixer 34 combines phase-controlled output signals 32, 32' producing mixed output signals 38 and 38' which are provided to the input of amplifiers 40 and 40' respectively. Amplifiers 40, 40' provide amplified output signals 42 and 42' respectively which are, in turn, applied to isolators 44 and 44'. Signals from isolators 44, 44' are applied to switch 46 which selects an output modality depending upon whether bipolar or quadrapolar therapy is being performed. Appropriate switched signals are provided to electrode connectors 48. In the preferred embodiment, switch 46 is a mechanical switch but the switching function could readily be performed by an electronic switch or electro-mechanical relay under control of microprocessor 60. A data/control bus 58, connected to microprocessor 60 is used to interconnect microprocessor 60 to other system components including a control panel 54 which contains all necessary controls, and an LCD display panel 56.

Figure 3:
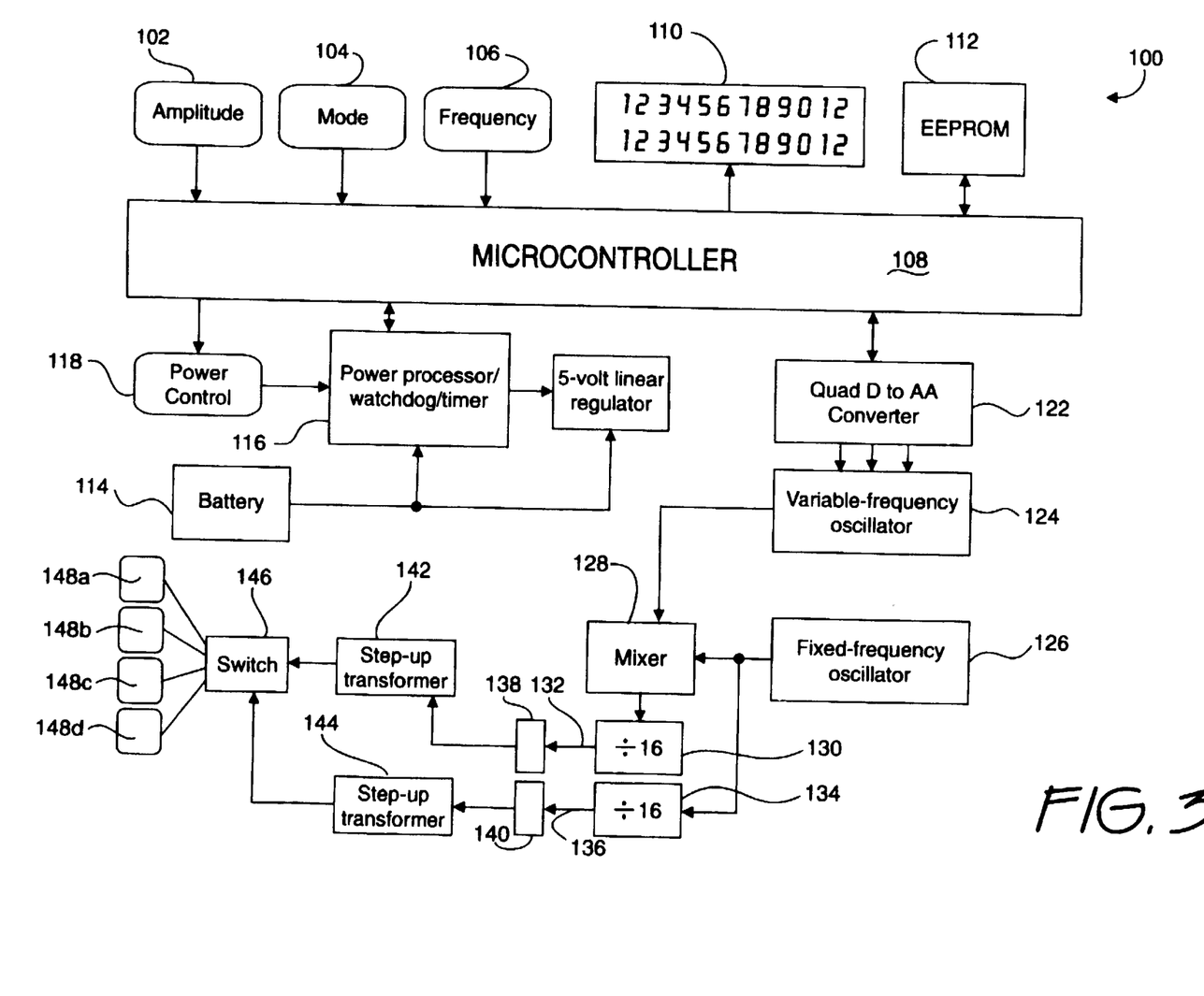
FIG. 3 is a functional block diagram of the interferential stimulator of the invention.

Referring now to FIG. 3, there is shown a detailed functional block diagram of the interferential stimulator of the present invention, generally at reference number 100. Three sets of control keys are located on the front panel (not shown) of the stimulator. These include: Amplitude adjustment keys 102, mode selection keys 104, and frequency adjustment keys 106. In the preferred embodiment, keys 102, 104 and 106 are momentary, normally open contacts appropriately debounced and applied to an input port of the microcontroller/microprocessor 108. It will be obvious that many other possibilities for switch types and contact configurations exist for implementing the key functions. The terms microprocessor and microcontroller will be used interchangeably hereinbelow. The microcontroller 108 chosen for purposes of disclosure is a Motorola MC68HC705C8. Any of a wide variety of microcontrollers from various manufacturers as are well know to those skilled in the art may be substituted for the MC68HC705C8 chip chosen for purposes of disclosure.

An alpha-numeric display 110, implemented as a liquid crystal display (LCD) with a display capability of two lines of 12 characters per line in the preferred embodiment, is also functionally connected to microcontroller 108.

A non-volatile memory 112 is also shown connected to microcontroller 108. In the preferred embodiment, memory 112 is implemented as an 8 kB EEPROM although implementations using other technologies and/or memory capacities are possible without departing from the true spirit of the invention. In alternate embodiments, a lithium or similar battery (not shown) may be used to back up the internal memory (RAM) of microcontroller 108 when the stimulator is in an off state.

Power for the stimulator is supplied by a self-contained battery pack 114. In the preferred embodiment battery pack 114 consists of six NiCd cells configured to provide a nominal 7.2 volt output. Sophisticated power control is implemented by a power gating/watchdog/timer circuit, 116. Power gating/watchdog/timer circuit 116, in combination with a power control key 118 are used to provide processor reset signals and to shut down the stimulator after a preprogrammed period of operation when a timed operation mode has been selected.

Digital-to-analog converters (DACs) 122 are used to convert digital output signals from microcontroller 108 into analog control voltages. In the preferred embodiment, quad, (4-channel), 8-bit DACs are used. Outputs of the DACs 122 are referenced to +5 volts which corresponds to a digital input of $255_{10}$.

A wide-range, variable frequency oscillator 124 is connected to the output of three of the four channels of DACs 122. Oscillator 124 provides a square-wave output whose frequency is controlled by the three analog control signals from DACs 122. The fourth analog control signal from DACs 122 is used to control the output signal amplitude. In the preferred embodiment, the output frequency of oscillator 124 is in the range of approximately 13 Hz to 2200 Hz. A divide-by-two flip-flop (not shown) connected directly to the output of variable-frequency oscillator 124 gives an effective operating range of approximately 6.5 Hz to 1100 Hz. The flip-flop (not shown) has been found necessary in the preferred embodiment because the particular oscillator circuit chosen has been found to exhibit unstable behavior at low frequencies (i.e., below 13 Hz). Also, oscillator 124 produces a train of very short pulses, not square waves. The flip-flop squares up the pulse train producing a perfect 50% duty cycle square wave which provides optimum mixing with the output of fixed-frequency oscillator 126. In alternate embodiments, the choice of a different oscillator circuit with better low-frequency stability would preclude the need for a divide-by-two flip-flop. Also, in alternate embodiments, no feedback from oscillator 124 to microcontroller 108 may be implemented. The output frequency of oscillator 124 could easily be sampled by microcontroller 108 and, by using such a feedback loop, even greater frequency stability could be obtained. The non-feedback implementation as disclosed in the preferred embodiment has be found to achieve satisfactory frequency stability for the intended application. The necessary hardware to support a feedback implementation is disclosed. However, in the preferred embodiment, feedback has not been implemented in software.

A second, fixed-frequency oscillator 126 provides a square-wave output of, in the preferred embodiment, approximately 68.8 kHz.

The output from both variable-frequency oscillator 124 and fixed-frequency oscillator 126 are provided at inputs of mixer 128. In the preferred embodiment, mixer 128 is implemented as an exclusive OR circuit performing as a single-bit adder. It will be obvious to those of skill in the art that there are numerous other ways to combine or mix plural digital signals which would be equally suitable for the application. The output of mixer 128 is a single pulse string whose frequency is the sum of the frequencies of the two input signals.

The output of mixer 128 is applied to a divide-by-sixteen counter, 130. The output of counter 130 is the "Variable Frequency Output Signal", 132. The output of fixed-frequency oscillator 126 is also applied to a second divide-by-sixteen counter, 134. The output of counter 134 is the "Fixed Frequency Output Signal", 136. Both output signals 132 and 136 are applied to the inputs of driver circuits, 138 and 140, respectively, in turn, the output signals from driver circuits 138 and 140 are applied to a the primary winding of a pair of step-up transformers, 142 and 144, respectively. The secondary windings of transformers 142 and 144 are applied to switch 146, and subsequently to electrodes 148a, 148b, 148c and 148d in the pattern selected by the setting of switch 146.

Figure 4A:
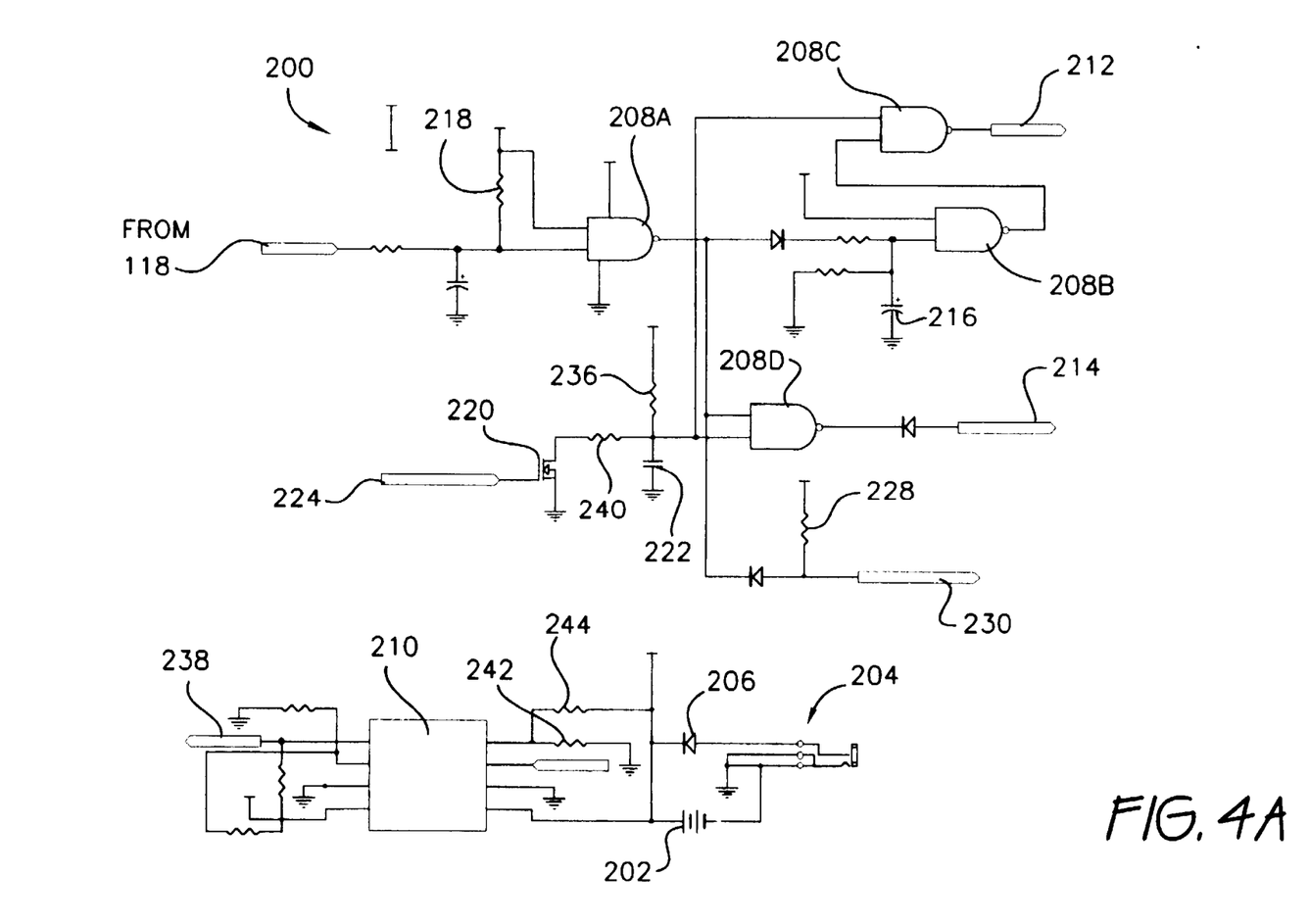
FIG. 4a is a schematic diagram of power management circuitry of the interferential stimulator.

Referring now to FIG. 4a there is shown a detailed schematic diagram of the power management circuitry of the preferred embodiment of the instant interferential stimulator. Main power to system circuitry is provided by a nickel-cadmium battery 202 consisting of six AA cells, which may be recharged by connecting a current-limited power source to battery charger (not shown) jack 204. Diode 206 prevents a reversed polarity on the charger plug from damaging the battery 202 thereby preventing a fire hazard. The charger (not shown) is expected to deliver a constant maximum current of 100 mA to the battery 202.

Battery power is constantly available to the power control circuitry built around the quad dual-input Schmitt-Trigger NAND gate IC 208a and the voltage regulator IC 210. This power control circuitry responds to a signal originating at the front-panel power control key 118 (FIG. 3). Assuming the stimulator is initially OFF, pressing the power key 118 causes the regulator gating signal 212 "RegGate" to be a logic-1 (on). When "RegGate" is on, regulator 210 supplies +5 volts to the connected system circuitry, including the microcontroller 108 (FIG. 3). As long as the power key 118 is pressed, regulator 210 remains active and the "ProcReset" signal 214 is a logic-0 (off), thus maintaining the microcontroller 108 in a RESET state.

When power key 118 is released, capacitor 227 begins charging through resistor 218. After a time delay of about a half-second, "ProcReset" 214 is released and microcontroller 108 is allowed to run. Simultaneously, capacitor 216 begins discharging through resistor 217. After a time delay of about 2 seconds, the output NAND 208b changes from a logic-0 to a logic-1 state.

At this point, it is expected that the microcontroller 108 has been running properly and has been creating "power-lock" pulses to appear at the gate of FET 220. If this is true, capacitor 222 will have been discharged, thus maintaining a logic-0 state at inputs to NANDs 208c and 208d. When the "power-lock" pulses 224 are so applied, the "RegGate" 212 signal will remain a logic-1, thus maintaining +5 volt power to the stimulator circuitry. This condition also assures that the "ProcReset" 214 signal will remain at a logic-1, thus allowing the microcontroller 108 to continue running. If the microcontroller 108 fails to begin running properly when "ProcReset" 214 is released, then, at the end of the 2-second delay mentioned above, inputs to NANDs 208c and 208d will be logic-1's and both the "RegGate" 212 and the "ProcReset" 214 signals will be logic-0, thus disabling +5 volt power to the remainder of the stimulator circuitry.

During normal operation, microcontroller 108 continuously generates pulses on "PwrLockPulse" line 224, thereby maintaining capacitor 222 in a discharged state. While capacitor 222 remains discharged, the stimulator's +5-volt power will remain on. If power key 118 (FIG. 3) is pressed while the stimulator is operating, it has no direct effect upon the "RegGate" 212 or "ProcReset" 214 signals. Diode 226 and pull-up resistor 228 allow the state of the power key 118 (FIG. 3) to be monitored by microcontroller 108 via I/O Port C, bit #5 (not shown), also called "PwrBtnState" 230. While the microcontroller's program (not shown) is running, microcontroller 108 polls this input (I/O Port C, bit #5, not shown) to determine if the operator wishes to turn off power. If a logic-1 state indicating that power key 118 is depressed is detected consistently across several polling samples, microcontroller 108 transfers compliance information (not shown) to the external EEPROM 112 (FIG. 3) memory and then waits for the operator to release power key 118. After power key 118 is released, microcontroller 108 simply stops generating "PwrLocPulse", 224. This allows capacitor 222 to charge through resistor 236. After a brief delay, inputs to NANDs 208c and 208d will become logic-1's, both the "RegGate" 212 and "ProcReset" 214 signals will be logic-0's, and system's +5-volt power will be shut off.

Figure 4B:
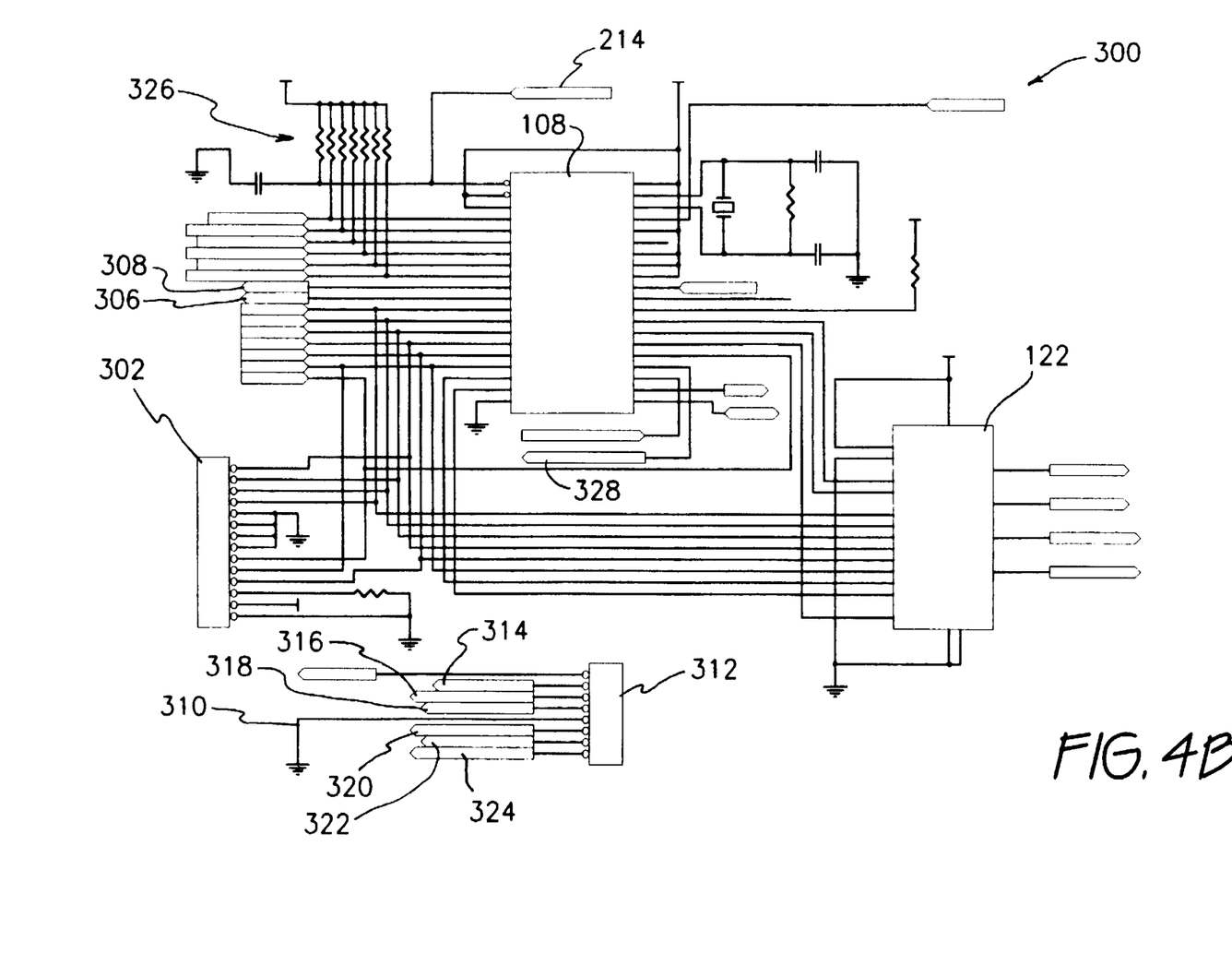
FIG. 4b is a schematic diagram of the microprocessor and peripheral circuitry of the interferential stimulator.

Referring now also to FIG. 4b, there is shown generally at reference number 300, a detailed schematic diagram of the microcontroller and peripheral control circuitry of the preferred embodiment of the instant stimulator. The microcontroller 108 chosen for purposes of disclosure currently is an 8-bit, 6805 microprocessor manufactured by Motorola. The program (not shown) for the operation of microcontroller 108 is stored in an internal PROM (not shown). Following power up and the release of the "ProcReset" 214 input, the program begins by performing a read-write test on the microprocessor 108's internal RAM (not shown) and a checksum test on the PROM (not shown) contents. If these tests fail, an attempt is made to report the problem to the operator with a message on the liquid crystal display (LCD) 110 (FIG. 3) connected via connector 302. In any event, the unit will subsequently shut down in the absence of "PwrLocPulse" 224. If both memory tests pass, microcontroller 108 initializes all I/O port pins. External circuitry connected to the I/O pins is thereby initialized and enabled. LCD 110 is tested for accessibility by using its "BUSY" line. If LCD 110 fails to properly acknowledge communications via the "BUSY" line, the stimulator will shut down. Zeros are next written into all four output modulation control DACs contained within integrated circuit 122. Note that no stimulator output signals can be generated until the microcontroller actively drives the "INIT1" 306 and "INIT2" 308 control lines to the proper logic states. This prevents spurious and possibly annoying output energy from being delivered to the electrodes 148 (FIG. 3) immediately after power-up before the processor is actively controlling the stimulator.

The condition of the 6-cell nickel-cadmium battery 202 is evaluated by circuitry within voltage regulator 210. The "LowBatt" signal 238 from regulator 210 is provided to the microcontroller 108 via I/O Port D, bit #2. Microcontroller 108 checks this input regularly during normal operation and checks it early in the start-up sequence. If battery 202 is low, microcontroller 108 briefly shows a message on LCD 110 (FIG. 3) and then shuts the stimulator off.

Before beginning routine operations, the manufacturer's name for the unit or other identifying indicia are momentarily shown on the liquid crystal display 110. Next, microcontroller 108 looks for previously stored compliance data in the external EEPROM 112 (FIG. 3). If compliance data is found, it is used to initialize internal microcontroller RAM variables (not shown) which will be updated with new compliance information during the forthcoming treatment.

For microcontroller 108, routine operations consist of making sure the unit shuts off automatically after a certain number of minutes of operation, monitoring the front-panel keys, updating the information displayed on the LCD, maintaining the internal variables used to store compliance information, checking for a low battery, driving the power-lock circuit, and driving the digital-to-analog converters (DACs) which modulate the electrode-driving output signals.

In the preferred embodiment, the stimulator will power itself down after 60 minutes of total running time following power-up. In some embodiments, the shut-off time may be programmed to be 15 minutes. The auto-shutoff feature is implemented in software and so may be easily changed without any change in the stimulator hardware.

The seven front-panel keys including power key 118, amplitude control keys 102, mode control keys 104 and frequency control keys 106 are normally-open momentary membrane-type switches with a common connection terminal (not shown) between them. This common terminal is connected to power ground through line 310. Signals from the other, non-commoned contacts from switches 118, 102, 104 and 106: "BTN AmpUp" 314, "BTN AmpDown" 316, "BTN ModeUp" 318, "BTN ModeDown" 320, "BTN FreqUp" 322 and "BTN FreqDown" 324 are connected to microcontroller 108 through connector 312. These six signals 314, 316, 318, 320, 322, 324 are connected to microcontroller 108 via I/O Port A. Each signal is also connected to an independent pull-up resistor, 326, to ensure that the corresponding microcontroller 108 input is a logic-1 whenever a given key switch is open (not depressed) and zero when that key switch is closed (depressed). The seventh key is the power control key 118 (FIG. 3). It connects to microcontroller 108 and the special power control circuitry as described hereinabove.

Liquid crystal display (LCD) module 110 interfaces to microcontroller 108 via I/O Port B, bits #0–5 and I/O Port C, bit #3. These connections are established through connector 302. The lines connected to I/O Port B constitute 6 bits out of an 8-bit bus which provides communications between the microcontroller and two peripheral devices, LCD 110 being one, the quad DAC 122 being the second. The 6 bits from I/O Port B include 4 LCD data bits and two LCD control wires. I/O Port C bit #3 is called "LCDEN", and serves as a strobe signal for the LCD 110. There is nothing unusual about the LCD display module 110. In the preferred embodiment, it is a character-oriented device which displays two lines of twelve characters each. It should be obvious to those having skill in the art that any number of different display technologies and/or configurations could be substituted.

Compliance information is retained in non-volatile EEPROM memory 112 (FIG. 3) when the stimulator is turned off. Compliance data from EEPROM 112 is copied into microcontroller RAM (not shown) when the unit is again turned on. At the end of a therapy session, updated compliance information is copied back to EEPROM 112 immediately before the stimulator is turned off. The compliance information maintained within the preferred embodiment consists of two basic quantities: the total number of minutes of use and the total number of uses. The stimulator will only add one to the uses counter if the unit is operated continuously for a minimum of one minute with the output amplitude set higher than zero. Subsequently, the minutes of use counter will increment once for every minute of operation during which the amplitude is set higher than zero. The operator can reset these two count values to zero by pressing a "secret" key combination on the front-panel keyboard during the first few seconds of operation after power-up. The operator can read these two count values on liquid crystal display 110 by pressing a second, simpler "secret" key combination on the front-panel keyboard any time during the first minute of operation after power-up. Maintenance and storage of additional compliance data such as modulation mode, is possible in alternate embodiments. EEPROM 112 has a capacity of 8 kB, far more capacity than is necessary to store the compliance data in the preferred embodiment, thus allowing for the storage of additional compliance parameters in the future without any hardware change being required.

The battery condition is determined by a simple threshold comparator integrated into the low-drop-out linear voltage regulator 210. The comparison threshold is set using external precision resistors 242 and 244. The threshold value was selected to ensure that the voltage regulator would still be able to regulate a +5-volt output when the battery 114 reached the predetermined threshold. Because nickel-cadmium (NiCad) batteries generally have an essentially flat discharge curve, their output voltage remains quite high until they are about to go dead. At that time, their terminal voltage falls off fairly rapidly, depending on loading. When the voltage output from 6-cell NiCad battery 114 starts to drop, it quickly reaches the low-battery detection threshold, and a logic-0 signal called "LowBatt" 238 is provided from regulator 210 to microcontroller 108. Microcontroller 108 rapidly shuts down the system in response to this signal so that +5-volt DC power will not be disrupted while the stimulator is running.

As long as microcontroller 108 is performing routinely, it toggles the "ProcPwrLock" signal 328, connected to I/O Port C, bit #4. Each time "ProcPwrLock" 328 changes state, from 0 to 1 or from 1 to 0, a pulse is produced. Each such pulse momentarily activates FET 220 causing it to rapidly discharge capacitor 222 low-value resistor 240. When FET 220 turns off between pulses, capacitor 222 begins to re-charge through high-value resistor 236. If capacitor 222 charges to a voltage above the switching threshold of the Schmitt-Trigger NAND gate 208c input, this will be interpreted by microprocessor 108 as either a system fault or a deliberate move to power down the system. In either case, the system +5-volt power will be turned off. Thus, the microcontroller must always toggle "ProcPwrLock" 328 at some minimum frequency to maintain its own power. The program code to accomplish this toggling is deliberately left out of the timer interrupt service routine so that the locking signal will disappear if the foreground task loop "crashes".

Using code driven by the interrupt service routine within microcontroller 108, the various output modulation modes are implemented. The output signals are, fundamentally, generated by two free-running oscillators, independent of the microcontroller 108.

Modulation of the generated output signals is accomplished by changing voltages at the output of each of four digital-to-analog converters (DACS) contained within integrated circuit 122. The inputs to DACs 122 are eight-bit digital signals presented to DACs 122 by means of an eight-bit data bus implemented on I/O Port B, as described previously. Three additional control signals are connected between microcontroller 108 and the quad DAC 122 at I/O Port C, bits #0–2. Two of these bits, labeled $A_0$ and $A_1$, allow selection of one DAC of the available four. The third bit, labeled "DACWR-", serves as a strobe for the quad DAC 122, signaling DAC 122 to capture the values of the data bits presented on the I/O Port B data bus. The output of all four DACs 122 are referenced to the +5 volt DC power supply, so a digital input value of $255_{10}$ corresponds to an analog output voltage of +5 volts.

By changing the voltage at the output of DACs 122, section "D", microcontroller 108 can change the amplitude of the electrode driving signals. The output of DACs 122, section "D" is labeled "DACPIN19".

Figure 4C:
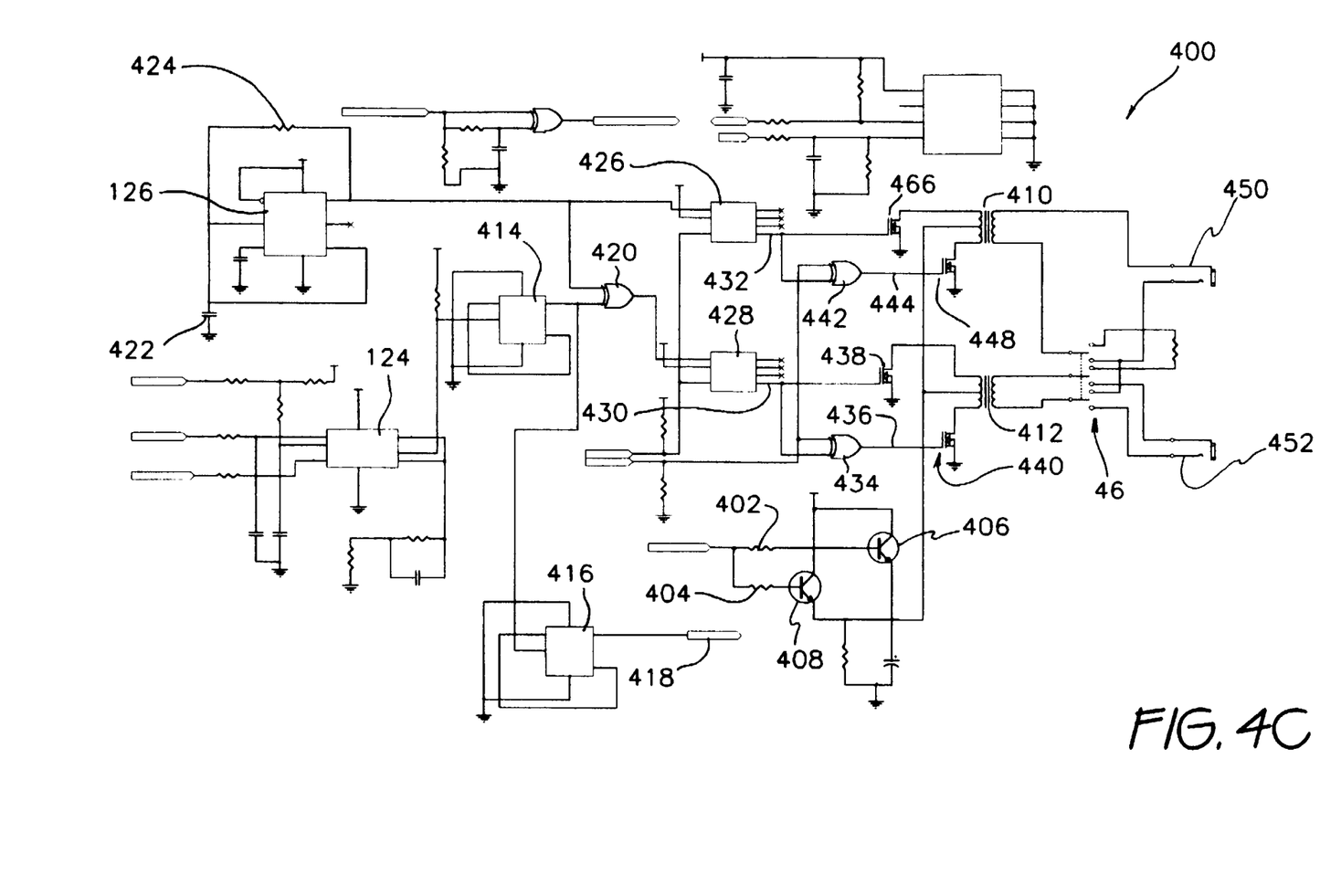
FIG. 4c is a schematic diagram of the signal generation and output circuitry of the interferential stimulator.

Referring now also to FIG. 4c, there is shown a detailed schematic diagram of the signal generation and output circuitry of the instant stimulator, generally at reference number 400. Resistors 402 and 404 are connected to emitter-follower circuits implemented by NPN transistors 406 and 408 respectively. Resisters 402 and 404 serve to convert the output voltage from DACs 122, section "D" into currents flowing through the bases of transistors 406 and 408. To improve efficiency, the emitter-follower pair formed by transistors 406 and 408 is powered directly from the main battery 114 (FIG. 3). The emitter-follower pair acts as a high-current, low-gain buffer amplifier, enabling microcontroller 108 to adjust the voltage appearing at the center tap terminals of the primary windings of final output transformers 410 and 412. Since the primary windings of transformers 410 and 412 are driven push-pull style by the N-channel FETs 438, 440, 446, 448 in cooperation with transistors 406 and 408, the positive voltage applied to the primary winding's center tap will determine the maximum amplitude of the AC signal generated at the secondary terminals of each of the transformers, 410, 412. There are efficiency limitations associated with this emitter-follower design, but it has been selected for the preferred embodiment because it is virtually indestructible. Other driver implementation such as switch-mode regulators, charge-pump devices, or other such devices and/or techniques as are well known to those of skill in the art could easily be substituted for the emitter-follower design chosen for purposes of disclosure.

The three remaining sections ("A", "B", "C") of DACs 122 are used to control variable frequency oscillator 124 (FIG. 3) implemented using an LM331A integrated circuit which functions as a charge-pump based oscillator. The three DACs 122 allow for microcontroller 108 to adjust the reference current source and apparent series resistance in the basic oscillator circuit. The functioning of an LM331A integrated circuit configured in this manner is described in detail in the manufacturer's data sheet for the device. By the output of three sections of DACs 122 as control inputs, the dynamic range of this oscillator 124 is significantly increased. Oscillator 124 operates well over a range from 26 Hertz to 4400 Hertz. The program code running on microcontroller 108 uses a look-up table (not shown) to control these three sections of DACs 122. A desired frequency selection number dialed in by the operator using frequency control keys 106 (FIG. 3), is used as an index into this look-up table. Each table entry contains three values, each value corresponding to one section of DACs 122. In the preferred embodiment, one section of DACs 122 is also used to sweep the output frequency back and forth around the user-selected frequency when certain modulation modes are selected.

The variable frequency oscillator 124 generates asymmetrical output pulses and it does not operate well at extremely low frequencies. To overcome this limitation, oscillator 124 is operated at a frequency twice the desired output frequency. The output of oscillator 122 is connected to flip-flop 414 which is used to divide the output pulse train by two, yielding a 50% duty-cycle square wave with a frequency range from 13 Hertz to 2200 Hertz which is considered ideal. A second flip-flop 416 divides the signal by two again, yielding an output signal called "MCIRQ-" 418 which has a frequency range from 6.5 Hertz to 1100 Hertz. Signal "MCIRQ-" 418 is applied to the "INTERRUPT" input on microcontroller 108 to accurately regulate the variable oscillator's 124 frequency by counting "MCIRQ-" 418. In alternate embodiments, the duration of the pulses of signal "MCIRQ-" 418 could be measured. The hardware for such measurements has been disclosed. However, in the preferred embodiment, the necessary software to implement the pulse measurement or counting has not been implemented.

The 13 Hz–2200 Hz, 50% duty cycle square wave signal generated at output of flip-flop 414 is applied to one input of an exclusive-OR gate 420. The other input to gate 420 is connected to the output from the fixed frequency oscillator 126. Fixed-frequency oscillator 126 is implemented using an TLC555C integrated circuit module configured as a free-running oscillator. Exclusive-OR gate 420 acts as a single-bit adder, effectively mixing the two input signals together and producing an output pulse train with a frequency equal to the sum of the two input frequencies. Each time either one of the inputs changes state independent of the other input, the output at gate 420 changes state. Occasionally, both inputs may change simultaneously, causing the output at gate 420 to remain unchanged, but this has not been found to be a statistically significant problem. Because the variable frequency oscillator 124 can be modulated, microcontroller 108 can control the frequency of the mixture product generated at the output of gate 420. It is important to note that whatever frequency is generated by the fixed oscillator 126, the frequency at the output of gate 420 will always differ from that frequency by an amount determined by half the frequency of the variable frequency oscillator 124. Because of this phenomenon, simple, less accurate R/C timing circuits can be used to implement both the variable frequency oscillator 124 and the fixed-frequency oscillator 126 without adversely affecting the overall performance of the stimulator.

The configuration of fixed frequency oscillator 126 is very simple. A CMOS version of the classic 555 timer is used to create a 50% duty-cycle square-wave oscillator. The free-running oscillation frequency is determined by timing capacitor 422 and feedback resistor 424. Both of these components have been selected to have good stability relative to both time and temperature. The nominal desired output frequency of oscillator 122 is 68.8 kilohertz, but the actual frequency may vary slightly from this without affecting the overall performance of the stimulator.

In addition to being mixed with output from the variable oscillator 124, the output of fixed frequency oscillator 126 is applied directly to the input of a 4-bit counter 426 which divides oscillator 126 output frequency by 16, nominally yielding a fixed 4300 Hertz output signal 432.

The "mixer" output signal at the output of gate 420 is also divided by 16 by the 4-bit counter 428, yielding a variable frequency output signal 430 in the range from 4300.8125 Hertz to 4437.5 Hertz. It will be obvious to those of skill in the art that other frequency combinations could easily be employed to achieve a similar therapeutic result.

Each of the two divider output signals 430, 432 described hereinabove is ultimately applied to a pair of electrodes 148a/148b, 148c/148d (FIG. 3) attached to the patient (not shown). The fixed 4300 Hertz signal 432 is also provided to the input of an inverter 442. Inverter 442 provides an output signal 444 which is 180° out-of-phase with input signal 432. These two complementary signals 432, 444 drive N-channel FETs 446 and 448, respectively. This causes current to flow alternately through one half and then the other half of the primary winding of step-up transformer 410. A symmetrical AC square wave is generated at the secondary winding of transformer 410, and it is this signal which drives one of the electrode pairs (148a, 148b) attached to the patient. As described above, the amplitude of the output square wave is dependent upon the positive DC voltage, set by microcontroller 108, which is applied to the center tap of the transformer 410's primary winding. The amplitude of the secondary winding voltage is also affected by the impedance of the connected electrode circuit and the primary/secondary turns ratio of transformer 410. It will be obvious to those skilled in the art that a variety of transformers could easily be employed by varying other circuit components and parameters accordingly.

Variable frequency signal 430 is also applied to the input of an inverter 434. Inverter 434 provides an output signal 436 which is 180° out-of-phase with input signal 430. These two complementary signals 430, 436 drive N-channel FETs 438 and 440, respectively. This causes current to flow alternately through one half and then the other half of the primary winding of step-up transformer 412. A symmetrical AC square wave is generated at the secondary winding of transformer 412, and it is this signal which drives the second electrode pair (148c, 148d) attached to the patient. As described above, the amplitude of the output square wave is dependent upon the positive DC voltage, set by microcontroller 108, which is applied to the center tap of the transformer 412's primary winding. The amplitude of the secondary winding voltage is also affected by the impedance of the connected electrode circuit and the primary/secondary turns ratio of transformer 412. Step-up transformers 410, 412 are identical in the preferred embodiment.

The electrode-driving signals from transformers 410 and 412 are connected to rocker switch 46 (FIG. 3), which then connects them to the electrode connection jacks 450 and 454. Switch 46 is a mode selector switch, and its function has been described hereinabove.

In the interferential mode, the two transformer output signals are always at slightly different frequencies, which is why they combine to produce a rotating electric current in the patient. The phase angle between the two signals is also always changing. The phase angle changes slowly when the variable oscillator 124 is set to a low frequency, rapidly when the variable oscillator 124 is set to a high frequency.

In the 2-electrode mode (non-interferential mode), the two transformer output signals are connected in series by switch 46, adding them directly to each other. As the phase angle between the two drive signals changes, the pulses at the active electrode jack 450, 452 widen and narrow repeatedly, with a pulse repetition rate of approximately 4300 Hertz.

Since other modifications and changes varied to fit a particular operating requirements and environment will be apparent to those skilled in the art, the invention is not considered limited to the example chosen for purposes of disclosure, and covers all changes and modifications which do not constitute a departure from the true spirit and scope of the invention.

Having thus described the invention, what is desired to be protected by Letters Patent is presented in the subsequent appended claims.

What is claimed is:

1. An interferential stimulation apparatus for providing a predetermined electrical signal to a user, comprising:

first signal source for providing a first signal, said first signal having a first frequency;

a second signal source for providing a second signal, said second signal having a second frequency, said second frequency being different from said first frequency;

control means operatively connected to said first signal source and to said second signal source for controlling at least one from the group of amplitude, frequency, phase, current, or pulse width of at least one of said first signal and said second signal, thereby generating a first controlled signal and a second controlled signal;

mixing means, operatively connected to said control means, for combining at least a portion said first controlled signal and at least a portion of said second controlled signal and producing a resultant signal having a frequency which is the sum of said first frequency and said second frequency;

electrode means operatively connected to said control means and to said mixing means for applying at least one of said first controlled signal, said second controlled signal, or said resultant signal to the skin of a person, said signal being an applied signal; and monitoring means operatively connected to said control means for recording information about said applied signal and retaining said recorded information within the stimulator.

2. The interferential stimulation apparatus for providing a predetermined electrical signal to a user as recited in claim 1, wherein said first signal is an alternating current voltage and said first frequency is approximately 4300 Hertz.

3. The interferential stimulation apparatus for providing a predetermined electrical signal to a user as recited in claim 1, wherein said second signal is a variable-frequency, alternating current voltage and said second frequency is in the range of approximately 13 Hertz to 2200 Hertz.

4. The interferential stimulation apparatus for providing a predetermined electrical signal to a user as recited in claim 1, further comprising:

amplifying means operative connected to said mixing means for increasing the level of at least one of said resultant signal, said first controlled signal, and said second controlled signal.

5. The interferential stimulation apparatus for providing a predetermined electrical signal to a user as recited in claim 4, further comprising:

isolation means operatively connected to said electrode means and to said amplifying means for providing electrical isolation between at least one of said resultant signal, said first controlled signal and said second controlled signal.

6. The interferential stimulation apparatus for providing a predetermined electrical signal to a user as recited in claim 5, wherein said isolation means comprises a transformer.

7. The interferential stimulation apparatus for providing a predetermined electrical signal to a user as recited in claim 1, wherein said control means further comprises a digital control means and at least one user-accessible switch operatively connected to said digital control means.

8. The interferential stimulation apparatus for providing a predetermined electrical signal to a user as recited in claim 1, further comprising an alpha-numeric display means.

9. The interferential stimulation apparatus for providing a predetermined electrical signal to a user as recited in claim 8, wherein said alpha-numeric display means is and LCD display having a display capability of at least twenty-four characters.

10. The interferential stimulation apparatus for providing a predetermined electrical signal to a user as recited in claim 9, wherein said at least twenty-four characters are arranged in a matrix, said matrix having two rows and twelve columns.

11. The interferential stimulation apparatus for providing a predetermined electrical signal to a user as recited in claim 1, wherein said monitoring means comprises a memory device.

12. The interferential stimulation apparatus for providing a predetermined electrical signal to a user as recited in claim 11, wherein said memory device comprises an EEPROM.

13. The interferential stimulation apparatus for providing a predetermined electrical signal to a user as recited in claim 12, wherein said EEPROM comprises an EEPROM having a storage capacity of at least 8000 bytes.

14. The interferential stimulation apparatus for providing a predetermined electrical signal to a user as recited in claim 1, further comprising a microcontroller operatively connected to at least one from the group of said first signal source, said second signal source, said control means, said mixing means and said monitoring means, said microcontroller further comprising a memory for retaining instructions, said instructions directing the operation of said microcontroller.

15. The interferential stimulation apparatus for providing a predetermined electrical signal to a user as recited in claim 14, wherein said microcontroller comprises a microprocessor.

16. The interferential stimulation apparatus for providing a predetermined electrical signal to a user as recited in claim 14, further comprising an interface operatively connected to said microcontroller.

17. The interferential stimulation apparatus for providing a predetermined electrical signal to a user as recited in claim 16, wherein said interface comprises a bi-directional interface.

18. The interferential stimulation apparatus for providing a predetermined electrical signal to a user as recited in claim 17, wherein said bi-directional interface comprises a serial interface.

* * * * *